US008153987B2

(12) United States Patent
Hurst et al.

(10) Patent No.: US 8,153,987 B2
(45) Date of Patent: Apr. 10, 2012

(54) AUTOMATED CALIBRATION METHODOLOGY FOR VUV METROLOGY SYSTEM (75) Inventors: Jeffrey B. Hurst, Cedar Park, TX (US); Matthew Weldon, Austin, TX (US); Phillip Walsh, Austin, TX (US); Cristian Rivas, Katy, TX (US); Dale A. Harrison, Austin, TX (US)

(73) Assignee: Jordan Valley Semiconductors Ltd., Migdal Ha'Emek (IL)

( * ) Notice: Subject to any disclaimer, the term of this patent is extended or adjusted under 35 U.S.C. 154(b) by 438 days.

(21) Appl. No.: 12/454,837

(22) Filed: May 22, 2009

(65) Prior Publication Data

US 2010/0294922 A1 Nov. 25, 2010

(51) Int. Cl.
*G12B 13/00* (2006.01)
(52) U.S. Cl. ............... 250/372; 250/252.1; 356/433; 356/455; 356/448
(58) Field of Classification Search .......... 250/372, 250/252.1; 356/445, 448, 433
See application file for complete search history.

(56) References Cited

U.S. PATENT DOCUMENTS

| | | |
|---|---|---|
| 3,091,154 A | 5/1963 | Hall |
| 3,160,752 A | 12/1964 | Bennett |
| 3,572,951 A | 3/1971 | Rothwarf et al. |
| 3,751,643 A | 8/1973 | Dill et al. |
| 3,825,347 A | 7/1974 | Kaiser |
| 4,029,419 A | 6/1977 | Schumann et al. |
| 4,368,983 A | 1/1983 | Bennett |

(Continued)

FOREIGN PATENT DOCUMENTS

CN 2430682 Y 5/2001

(Continued)

OTHER PUBLICATIONS

Sendlebach, et al. "Integrated scatterometry in high volume manufacturing for polysilicon gate etch control," Metrology, Inspection, and Microlithography, edited by Chas N. Archie, Proc. of SPIE vol. 6152, published 2006.*

(Continued)

*Primary Examiner* — David Porta
*Assistant Examiner* — Yara Green
(74) *Attorney, Agent, or Firm* — D. Kligler IP Services Ltd.

(57) ABSTRACT

A calibration pad having multiple calibration sites is provided. A particular calibration site may be utilized until that particular site has been determined to have become unacceptable for further use, for example from contamination, in which case the calibration processes may then move to use a different calibration site(s) on the calibration pad(s). A variety of techniques may be utilized to provide the determination that a site is no longer acceptable for use. Movement may thus occur over time from site to site for use in a calibration process. A variety of criteria may be established to determine when to move to another site. Though the designation of a site as "bad" may be based upon measured reflectance data, other criteria may also be used. For example, the number of times a site has been exposed to light may be the criteria for designating a site as bad. Alternatively the cumulative exposure of a site may be the criteria. Further, the plurality of calibration sites that are provided on the single calibration pad may be pre-evaluated so as to initially screen out unacceptable calibration sites prior to use. The techniques provided may be utilized in calibration processes which utilize a single calibration sample or processes which require a plurality of calibration samples.

18 Claims, 6 Drawing Sheets

U.S. PATENT DOCUMENTS

| | | | |
|---|---|---|---|
| 4,645,349 A | 2/1987 | Tabata | |
| 4,729,657 A | 3/1988 | Cooper et al. | |
| 4,837,603 A | 6/1989 | Hayashi | |
| 4,899,055 A | 2/1990 | Adams | |
| 4,984,894 A | 1/1991 | Kondo | |
| 5,042,949 A | 8/1991 | Greenberg et al. | |
| 5,045,704 A | 9/1991 | Coates | |
| 5,120,966 A | 6/1992 | Kondon | |
| 5,128,549 A | 7/1992 | Kaye | |
| 5,182,618 A | 1/1993 | Heinonen | |
| 5,241,366 A | 8/1993 | Bevis et al. | |
| 5,251,006 A | 10/1993 | Hongis et al. | |
| 5,357,448 A | 10/1994 | Stanford | |
| RE34,783 E | 11/1994 | Coates | |
| 5,388,909 A | 2/1995 | Johnson et al. | |
| 5,440,141 A | 8/1995 | Horie | |
| 5,452,091 A | 9/1995 | Johnson | |
| 5,486,701 A | 1/1996 | Norton et al. | |
| 5,493,401 A | 2/1996 | Horie et al. | |
| 5,581,350 A | 12/1996 | Chen et al. | |
| 5,607,800 A | 3/1997 | Ziger | |
| 5,608,526 A | 3/1997 | Piwonka-Corle et al. | |
| 5,686,993 A | 11/1997 | Kokubo et al. | |
| 5,747,813 A | 5/1998 | Norton et al. | |
| 5,754,296 A | 5/1998 | Law | |
| 5,771,094 A | 6/1998 | Carter | |
| 5,777,733 A | 7/1998 | Radziuk | |
| 5,781,304 A | 7/1998 | Kotidis et al. | |
| 5,784,167 A | 7/1998 | Ho | |
| 5,798,837 A | 8/1998 | Aspnes et al. | |
| 5,805,285 A | 9/1998 | Jons et al. | |
| 5,867,276 A | 2/1999 | McNeil | |
| 5,880,831 A | 3/1999 | Buermann et al. | |
| 5,900,939 A | 5/1999 | Aspnes et al. | |
| 5,903,351 A | 5/1999 | Jeong et al. | |
| 5,917,594 A | 6/1999 | Norton | |
| 5,991,022 A | 11/1999 | Buermann et al. | |
| 6,052,401 A | 4/2000 | Wieser et al. | |
| 6,091,485 A | 7/2000 | Li et al. | |
| 6,122,052 A | 9/2000 | Barnes et al. | |
| 6,128,085 A | 10/2000 | Buermann et al. | |
| 6,129,807 A | 10/2000 | Grimbergen et al. | |
| 6,181,427 B1 | 1/2001 | Yarussi et al. | |
| 6,184,529 B1 | 2/2001 | Contini | |
| 6,184,984 B1 | 2/2001 | Lee | |
| 6,226,086 B1 | 5/2001 | Hollbrook et al. | |
| 6,261,853 B1 | 7/2001 | Howell et al. | |
| 6,265,033 B1 | 7/2001 | Hilliard et al. | |
| 6,275,292 B1 | 8/2001 | Thakur et al. | |
| 6,278,519 B1 | 8/2001 | Rosencwaig et al. | |
| 6,297,880 B1 | 10/2001 | Rosencwaig et al. | |
| 6,304,326 B1 | 10/2001 | Aspnes et al. | |
| 6,313,466 B1 | 11/2001 | Olsen et al. | |
| 6,340,602 B1 | 1/2002 | Johnson et al. | |
| 6,361,646 B1 | 3/2002 | Bibby et al. | |
| 6,392,756 B1 | 5/2002 | Li et al. | |
| 6,411,385 B2 | 6/2002 | Aspnes et al. | |
| 6,414,302 B1 | 7/2002 | Freeouf | |
| 6,417,921 B2 | 7/2002 | Rosencwaig et al. | |
| 6,433,878 B1 | 8/2002 | Niu et al. | |
| 6,453,006 B1 | 9/2002 | Koppel | |
| 6,485,872 B1 | 11/2002 | Rosenthal et al. | |
| 6,525,829 B1 | 2/2003 | Powell et al. | |
| 6,549,279 B2 | 4/2003 | Adams et al. | |
| 6,556,303 B1 | 4/2003 | Rangaran et al. | |
| 6,572,951 B2 | 6/2003 | Hasegawa et al. | |
| 6,580,510 B2 | 6/2003 | Nawracala | |
| 6,590,656 B2 | 7/2003 | Xu et al. | |
| 6,608,690 B2 | 8/2003 | Niu et al. | |
| 6,630,673 B2 | 10/2003 | Khalil et al. | |
| 6,630,996 B2 | 10/2003 | Rao et al. | |
| 6,633,831 B2 | 10/2003 | Nikoonahad et al. | |
| 6,643,354 B2 | 11/2003 | Koppel | |
| 6,657,737 B2 | 12/2003 | Kimba et al. | |
| 6,665,075 B2 | 12/2003 | Mittleman et al. | |
| 6,710,865 B2 | 3/2004 | Forouhi et al. | |
| 6,713,775 B2 | 3/2004 | Chelvayohan et al. | |
| 6,721,052 B2 | 4/2004 | Zhao et al. | |
| 6,734,968 B1 | 5/2004 | Wang et al. | |
| 6,765,676 B1 | 7/2004 | Buermann | |
| 6,768,785 B2 | 7/2004 | Koppel | |
| 6,801,309 B1 | 10/2004 | Nelson | |
| 6,879,395 B2 | 4/2005 | Oka et al. | |
| 6,891,626 B2 | 5/2005 | Niu et al. | |
| 6,897,456 B2 | 5/2005 | Hasegawa et al. | |
| 6,897,807 B2 | 5/2005 | Kishigami et al. | |
| 6,934,025 B2 | 8/2005 | Opsal et al. | |
| 6,982,792 B1 | 1/2006 | Woollam | |
| 6,987,832 B2 | 1/2006 | Koppel | |
| 7,026,165 B2 | 4/2006 | DeGrandpre | |
| 7,026,626 B2 | 4/2006 | Harrison | |
| 7,061,614 B2 | 6/2006 | Wang et al. | |
| 7,067,818 B2 | 6/2006 | Harrison | |
| 7,072,050 B2 | 7/2006 | Kimba et al. | |
| 7,126,131 B2 | 10/2006 | Harrison | |
| 7,130,029 B2 | 10/2006 | Wack et al. | |
| 7,189,973 B2 | 3/2007 | Harrison | |
| 7,224,471 B2 | 5/2007 | Bischoff et al. | |
| 7,242,477 B2 | 7/2007 | Mieher et al. | |
| 7,271,394 B2 | 9/2007 | Harrison | |
| 7,282,703 B2 | 10/2007 | Walsh et al. | |
| 7,342,235 B1 | 3/2008 | Harrison et al. | |
| 7,399,975 B2 | 7/2008 | Harrison | |
| 7,485,869 B2 | 2/2009 | Harrison et al. | |
| 7,511,265 B2 | 3/2009 | Walsh et al. | |
| 7,579,601 B2 | 8/2009 | Harrison | |
| 7,643,666 B2 | 1/2010 | Setija et al. | |
| 7,684,037 B2 | 3/2010 | Harrison et al. | |
| 2001/0055118 A1 | 12/2001 | Nawracala | |
| 2002/0030826 A1 | 3/2002 | Chalmers et al. | |
| 2002/0110218 A1 | 8/2002 | Koppel | |
| 2002/0126277 A1 | 9/2002 | Norton | |
| 2002/0149774 A1 | 10/2002 | McAninch | |
| 2002/0154302 A1 | 10/2002 | Rosencwaig | |
| 2002/0179864 A1 | 12/2002 | Fielden | |
| 2002/0179867 A1 | 12/2002 | Fielden | |
| 2002/0180961 A1 | 12/2002 | Wack | |
| 2002/0180985 A1 | 12/2002 | Wack | |
| 2002/0180986 A1 | 12/2002 | Nikoonahad | |
| 2002/0182760 A1 | 12/2002 | Wack | |
| 2002/0190207 A1 | 12/2002 | Levy | |
| 2003/0011786 A1 | 1/2003 | Levy | |
| 2003/0071996 A1 | 4/2003 | Wang et al. | |
| 2003/0081201 A1 | 5/2003 | Shibata et al. | |
| 2004/0032593 A1 | 2/2004 | Venugopal | |
| 2004/0052330 A1 | 3/2004 | Koppel | |
| 2004/0150820 A1 | 8/2004 | Nikoonahad et al. | |
| 2004/0218717 A1 | 11/2004 | Koppel | |
| 2005/0002037 A1 | 1/2005 | Harrison | |
| 2005/0036143 A1* | 2/2005 | Huang | 356/369 |
| 2006/0001885 A1 | 1/2006 | Hertzsch et al. | |
| 2007/0030488 A1 | 2/2007 | Harrison | |
| 2007/0181793 A1 | 8/2007 | Harrison | |
| 2007/0181795 A1 | 8/2007 | Walsh et al. | |
| 2007/0182970 A1 | 8/2007 | Harrison | |
| 2007/0215801 A1 | 9/2007 | Walsh et al. | |
| 2008/0042071 A1 | 2/2008 | Harrison | |
| 2008/0073560 A1 | 3/2008 | Harrison et al. | |
| 2008/0181793 A1 | 7/2008 | Mistry et al. | |
| 2008/0246951 A1 | 10/2008 | Walsh et al. | |
| 2009/0002711 A1 | 1/2009 | Harrison | |
| 2009/0248074 A1 | 10/2009 | Kliegman | |
| 2010/0051822 A1 | 3/2010 | Harrison | |

FOREIGN PATENT DOCUMENTS

| | | |
|---|---|---|
| JP | 10160572 A | 6/1998 |
| JP | 2000205966 | 7/2000 |
| JP | 2000249600 | 9/2000 |
| JP | 2002243381 | 8/2002 |
| JP | 03202266 A | 7/2003 |
| JP | 03232681 A | 8/2003 |
| WO | 9902970 A1 | 1/1999 |

OTHER PUBLICATIONS

U.S Appl. No. 12/876,242 Official Action dated Nov. 19, 2010.
U.S. Appl. No. 12/590,151 Official Action dated Mar. 17, 2011.

U.S. Appl. No. 12/876,242 Official Action dated May 20, 2011.
U.S. Appl. No. 12/834,939 Official Action dated Jun. 10, 2011.
U.S. Appl. No. 12/590,151 Official Action dated Jun. 25, 2010.
US Re-Examination Application # 90/009,409 Official Action dated Jun. 18, 2010.
Chinese Patent Application No. 200480027513.6 Official Action dated Jul. 18, 2008.
US Re-Examination Application # 90/009,320 Official Action dated Sep. 25, 2009, and Notice of Intent to Issue Re-Exam Certificate dated Jun. 23, 2010.
US Re-Examination Application # 95/000,535 Official Action dated May 14, 2010.
U.S. Appl. No. 10/930,339 Official Action dated Sep. 29, 2009.
U.S. Appl. No. 10/930,339 Official Action dated Jan. 18, 2007.
U.S. Appl. No. 10/930,339 Official Action dated Sep. 6, 2007.
U.S. Appl. No. 10/930,339 Official Action dated Apr. 18, 2008.
U.S. Appl. No. 10/930,339 Official Action dated Nov. 13, 2008.
Das et al., "Image Evaluation of the High-Resolution VUV Spectrometer at SURF II by Ray Tracing", Journal of Research of the National Institute of Standards and Technology, vol. 103, No. 5, pp. 483-495, Sep.-Oct. 1998.
Request for Ex Parte Reexamination for US Patent # 7,067,818 filed Feb. 11, 2009.
Request for Ex Parte Reexamination for US Patent # 7,067,818 filed Feb. 12, 2010.
Request for Ex Parte Reexamination for US Patent # 7,026,626 filed Nov. 7, 2008.
Japanese Patent Application # 528098/06 Official Action dated Jun. 15, 2010 (including English translation).
Rivas, "Optical Characterization of Hafnium-Based High-K Dielectric Films Using Vacuum Ultraviolet Reflectometry", XV International Conference on Vacuum Ultraviolet Radiation Physics, 2007, 6 pgs.
Bloomstein et al., "Contamination Rates of Optical Surface At 157NM in the Presence of Hydrocarbon Impurities", Optical Microlithography XV, Proceedings of the SPIE, vol. 4691, 2002, 15 pgs.
Okoroanyanwu et al., "Contamination Monitoring and Control on ASML MS-VII 157nm Exposure Tool", Optical Microlithography XVII, Proceedings of the SPIE, vol. 5377, 2004, 13 pgs.
"Optical Characterization of Molecular Contaminant Films" Photonics Tech Briefs, 2007, 2 pgs.
Aspnes, "The Accurate Determination of Optical Properties by Ellipsometry", Handbook of Optical Constants of Solids, vol. 1, ed. D, Academic Press, 1998, 5 pgs.
Press et al., "Numerical Recipes in C" The Art of Scientific Computing, Second Edition, 1992, 15.5 Nonlinear Models, pp. 681-688.
Jellison et al, "Parameterization of the Optical Functions of Amorphous Materials in the Interband Region", Applied Physics Letter, vol. 69, 1996, 3 pgs.
Jellison et al, "Erratum: Parameterization of the Optical Functions of Amorphous Materials in the Interband Region", Applied Physics Letter, vol. 69, 1996, 1 pg.

Field et al., "Method of Using the Reflectance Ratios of Different Angles of Incidence for the Determination of Optical Constants", Applied Optics, vol. 10, No. 6, Jun. 1971, 4 pgs.
Hunter et al., "Thickness of Absorbing Films Necessary to Measure Their Optical Constants Using the Reflectance-Vs-Angle-of-Incidence Method", Journal of the Optical Society of America, vol. 64, No. 4, Apr. 1874, 5 pgs.
Hunter et al., "Journal of the Optical Society of America", Optical Society of America, vol. 55, No. 10, Part 1, Oct. 1965, 8 pgs.
Rubloff, "Surface Reflectance Spectroscopy System", Technical Disclosure, Ip.com, www.ip.com, May 1, 1977, 5 pgs.
McPherson Product Brochure "Reflectometer for Sample Analysis," McPherson, Inc., Massachusetts, Published Prior to Sep. 23, 2003, 1-2 pps.
McPherson Product Brochure "Spectral Reflectometer," McPherson, Inc., Massachusetts, Nov. 12, 2001, 1 pg.
McPherson Product Brochure "VUVaS Spectrophotometers for 115 nm to >380 nm," McPherson, Inc., Massachusetts, Published Prior to Sep. 23, 2003, 1-4 pps.
McPherson Product Brochure "VUVaS Spectrophotometers, Made to Measure 115-380 nm," McPherson, Inc., Massachusetts, Published Prior to Sep. 23, 2003, 1-8 pps.
Acton Research Product Brochure "Acton Research Purged CAMS Optical Measurement System," Acton Research Corporation, Massachusetts, Published Prior to Sep. 23, 2003, 1-2 pps.
"The Thin Film tool for next generation lithography at 157nm," Web page from http://www.sopra-sa.com, Sopra, Printed From Internet on Feb. 19, 2002, 1 pg.
"SE and GXR combined on the same instrument," Web page from http://www.sopra-sa.com, Sopra, Printed From Internet on Feb. 19, 2002, 1 pg.
"The ideal Thin Film characterization unit for Development and Pilot Line environment," Web page from http://www.sopra-sa.com, Sopra, Printed From Internet on Feb. 19, 2002, 1 pg.
"VUV-VASE™, The Award Winning VUV-VASE™ is the latest addition to our line of Spectroscopic Ellipsometers," Web pages from http://www.jawoolam.com, J.A. Woollam Company, Nebraska, Printed From Internet on Nov. 5, 2002, 1-2 pps.
"Vacuum UV Spectroscopic Ellipsometers," Web pages from http://www.sentech.de, Sentech Instruments, Printed From Internet on Feb. 20, 2002, 1-3 pps.
Harrison et al., copending application, entitled "Contamination Monitoring and Control Techniques for Use With an Optical Metrology Instrument", filed Nov. 16, 2006, 53 pgs.
Walsh, copending application, entitled "Method and Apparatus for Using Multiple Relative Reflectance Measurements to Determine Properties of a Sample Using Vacuum Ultra Violet Wavelengths", filed Feb. 28, 2008, 43 pgs.
Search Report, PCT/US2007/010003, Dec. 17, 2008, 3 pgs.
Search Report; PCT/USO4/30859; 13 pgs.
U.S. Appl. No. 12/592,641 Official Action dated Aug. 20, 2010.
JP Patent Application # 528098/06 Official Action dated Aug. 30, 2011.
U.S. Appl. No. 12/854,917 Official Action dated Jul. 28, 2011.

* cited by examiner

FIG. 10

AUTOMATED CALIBRATION METHODOLOGY FOR VUV METROLOGY SYSTEM

TECHNICAL FIELD

The present application relates to the field of optical metrology and more specifically to an optical metrology method for automated calibration that may be operated at wavelengths that include the vacuum ultraviolet (VUV) range.

BACKGROUND

Optical reflectometry techniques have long been employed in process control applications in the semiconductor manufacturing industry due to their non-contact, non-destructive and generally high-throughput nature. The continuous push towards developing smaller devices comprised of thinner layers and the introduction of complicated new materials has challenged the sensitivity of such instrumentation. As a result, this has necessitated an effort to develop optical reflectometry equipment utilizing shorter vacuum ultraviolet (VUV) wavelengths (below 200 nm), where greater sensitivity to subtle changes in material properties may be realized.

Common tools used in optical metrology techniques are reflectometry and ellipsometry. Ellipsometry is generally regarded as consisting of a "richer" dataset, including a measurement of two quantities per wavelength/incident angle. On the other hand, reflectometers are more robust due to less complex hardware configurations, have faster measurements, and typically have a smaller footprint. Generally speaking, if both technologies are capable of solving a given metrology problem, the reflectometer is a more cost effective choice for a high volume production environment.

Contamination of optical surfaces like windows and mirrors is a serious impediment to the operation of optical instruments in the VUV range. Moisture and residual molecules, particularly hydrocarbon compounds, may deposit on such surfaces over time dramatically reducing their performance. These materials may form as a function of exposure to environment and/or out-gassing materials. Additionally, VUV and DUV radiation from the optical metrology tool itself may cause the formation of a contaminant film by reacting with accumulated airborne or out-gassed contaminants via a photo-deposition process. These effects have formed the focus of previous investigations owing to their impact on the design, development and performance of 193 and 157 nm lithographic exposure tools.

When present on the surfaces of samples under investigation, contaminate layers may significantly contribute to measured optical responses in the VUV yielding inaccurate and/or erroneous results. These effects are of particular concern when the samples are comprised of ultra thin films (<100 Å), whose thicknesses may themselves be comparable to the thicknesses of the contaminate layers. Airborne molecular contaminants (AMC) deposit on the surfaces of such samples significantly affecting reflectance in the VUV region. As used herein, AMC refers not only to typical contaminants deposited on samples, but also photo-deposited contaminants.

Reflectometer calibration in the VUV is difficult since reliable absolute reflectance standards do not exist and could not necessarily be maintained. In the past, new methods were developed to overcome these issues, such as for example in U.S. Pat. Nos. 7,282,703 and 7,511,265 and U.S. patent application Ser. Nos. 10/930,339, 11/789,686 and 12/072,878, the disclosures of which are all expressly incorporated by reference in their entirety. Some of these methods to calibrate reflectometers involved utilizing two calibration samples, measuring the intensity from both samples and analyzing the ratio of the two samples spectra to determine the properties of the samples and their absolute reflectances. In one embodiment, the calibration samples may be comprised of, but are not limited to, a bare silicon substrate with a native oxide layer and/or a 1000 Å SiO2 layer on a silicon substrate. This is only an exemplary composition of calibration samples. The techniques used previously work very well over a range of AMC buildup on calibration sites.

In the case where the thickness of deposited AMC exceeds some value, for example >40 Å, then the calibration sample measurements may be less accurate. This may be attributed to several reasons. For example, the AMC may be deposited over time in such a manner that an ever increasing fraction of the incident light becomes diffusely reflected. This could result in an error in the analysis of the measured spectrum. Or, the properties of the AMC film may not be uniform as a function of the film thickness. An inexact understanding of the optical properties of the AMC film, such as the case where the film consists of different components, could also lead to less accurate measurements.

In the operation of a VUV metrology instrument, previously disclosed methods provided techniques for minimizing, controlling and removing the deposited AMC layers that accumulated over time, such as for example in U.S. Pat. No. 7,342,235 and U.S. patent application Ser. Nos. 11/600,414 and 11/600,477, the disclosures of which are all expressly incorporated by reference in their entirety to overcome these issues. Though the previously described techniques provided an accurate means of calibration of a VUV optical metrology instrument, the measurements remained valid only over a specific range of deposited AMC thicknesses.

Calibration of the metrology equipment may also be dependant on the tool user. The equipment operator may have to continually check on the thickness of the AMC layers and determine if the layers were thick enough to compromise calibration accuracy. It would be beneficial to an automated semiconductor manufacturing environment if the responsibility of equipment calibration was shifted from the tool user to an automated system.

SUMMARY

A calibration pad having multiple calibration sites is provided. A particular calibration site may be utilized until that particular site has been determined to have become unacceptable for further use, for example from contamination, in which case the calibration processes may then move to use a different calibration site on the calibration pad. A variety of techniques may be utilized to provide the determination that a site is no longer acceptable for use. Movement may thus occur over time from site to site for use in a calibration process. A variety of criteria may be established to determine when to move to another site. Though the designation of a site as "bad" may be based upon measured reflectance data, other criteria may also be used. For example, the number of times a site has been exposed to light may be the criteria for designating a site as bad. Alternatively the cumulative exposure of a site may be the criteria. Further, the plurality of calibration sites that are provided on the single calibration pad may be pre-evaluated so as to initially screen out unacceptable calibration sites prior to use. The techniques provided may be utilized in calibration processes which utilize a single calibration sample or processes which require a plurality of calibration samples.

In one embodiment, a method of evaluating an optical metrology tool is provided. The method includes utilizing an optical tool characterization pad for use in assisting in the evaluation of an optical metrology tool and providing multiple characterization sites of a similar characterization structure upon the characterization pad. The method may further include designating at least some of the characterization sites as either acceptable for use or not, wherein based upon the designation, after the designation at least some of the characterization sites are not utilized for evaluation of the optical metrology tool.

In another embodiment, a method of calibrating an optical metrology tool is provided. The method may include providing a calibration pad for use in a calibration process of the optical metrology tool and partitioning the calibration pad into a plurality of calibration sites, the calibration sites having similar calibration structures. The method may further include utilizing a first calibration site of the calibration pad for calibrating the optical metrology tool and detecting that the first calibration site does not satisfy a criteria for use of the first calibration site. The method also includes switching from use of the first calibration site to use of a second calibration of the calibration pad for calibrating the optical metrology tool based upon the detection of the first calibration site not satisfying the criteria.

In still another embodiment, a pad for use in characterizing an optical metrology tool is provided. The pad may include a first region of the pad at which optical measurements may be obtained, the first region comprising characterization structures constructed to be used for characterizing the optical metrology tool. The pad further includes a plurality of sub-regions of the pad. The sub-regions may be a plurality of characterization sites which are sized such that separate optical measurements may be obtained from different ones of the characterization sites so that at least some of the characterization sites may be designated unacceptable for use in the characterization of the optical metrology tool while still allowing use of other of the characterization sites for characterizing the optical metrology tool.

As described below, other features and variations can be implemented, if desired, and related systems can be utilized, as well.

DESCRIPTION OF THE DRAWINGS

A more complete understanding of the present invention and advantages thereof may be acquired by referring to the following description taken in conjunction with the accompanying drawings, in which like reference numbers indicate like features. It is noted that the appended drawings illustrate only exemplary embodiments of the techniques described herein and are, therefore, not to be considered limiting of its scope, for the techniques may admit to other equally effective embodiments.

DETAILED DESCRIPTION

Single crystal silicon wafers have long been used as calibration standards for reflectometers operating in the DUV-NIR. They have proved a sensible choice, as they are ubiquitous, controllably manufactured and optically well characterized in this spectral region. When employed for the calibration of reflectometers operating at wavelengths longer than about 250 nm silicon wafers work well since the underlying assumptions regarding their physical properties are relatively insensitive to error in this wavelength region. In other words, errors in the assumed thickness of the native oxide layer and/or AMC on the surface of the wafer do not significantly influence the expected reflectance of the sample and hence do not negatively impact the accuracy of the calibration process.

Figure 1:
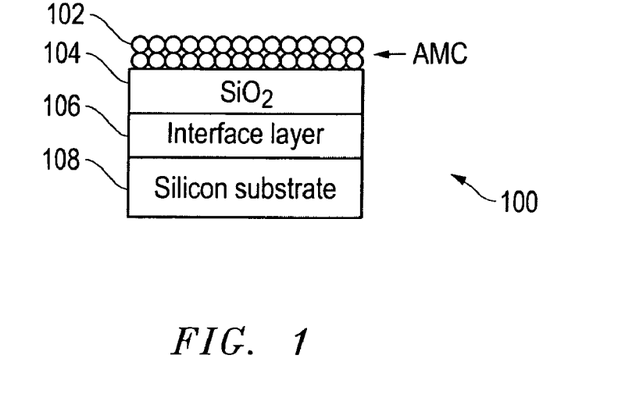
FIG. 1 is an exemplary typical calibration sample with acceptable AMC build-up.

In FIG. 1, an embodiment of a typical calibration sample 100 with an acceptable AMC build-up is depicted. The airborne molecular contaminants are deposited on the calibration sample in a planar fashion. This level deposit structure is well described by an optical model and yields a good fit between the measured and calculated calibration pad ratios. With the techniques described herein, it is not required that the film be deposited in a planar fashion in order to achieve "good" calibration results. Preferably, it is more important that the measured pad ratio be well described by the optical models used during its analysis. Layer 102 illustrates the planar build-up of the airborne molecular contaminants. Layer 104 represents the silicon dioxide (SiO2) top layer in a typical calibration sample. Layer 106 exemplifies the interface layer in a typical calibration sample. Layer 108 embodies the base silicon substrate layer in a typical calibration sample. This is only an exemplary composition of a calibration sample.

Figure 2:
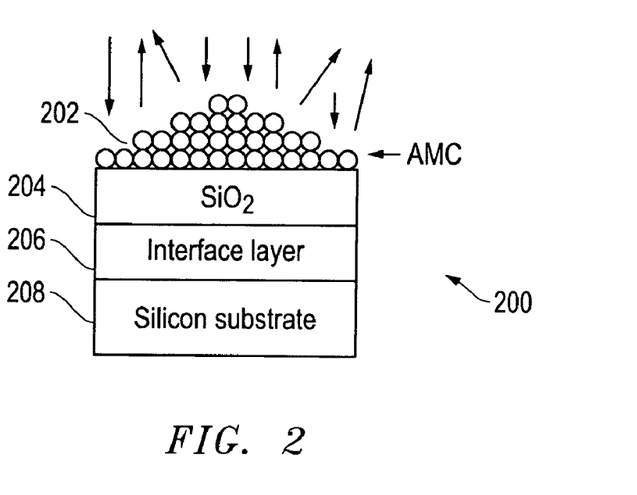
FIG. 2 is an exemplary typical calibration sample with unacceptable AMC build-up.

In FIG. 2, an example of a typical calibration sample 200 with an unacceptable AMC build-up is depicted. The AMC is deposited in a non-planar fashion. The uneven surface of the sample results in a scattering of the incident light beam and a loss of specularly reflected signal. This behavior may not be well described by the optical models utilized during analysis and could result in a poor fit between the calculated and measured pad ratio. The resultant calibration may be presumed to be inaccurate. Layer 202 illustrates the non-planar build-up of the airborne molecular contaminants. Layer 204 represents the silicon dioxide (SiO2) top layer in a typical calibration sample. Layer 206 exemplifies the interface layer in a typical calibration sample. Layer 208 embodies the base silicon substrate layer in a typical calibration sample. This is only an exemplary composition of a calibration sample and it will be recognized that many other calibration structures may be utilized. For example the calibration structure may be a multi-layered structure or alternatively a single layer structure. Also as will be recognized by those in the art, other materials may be utilized for the calibration structure layer(s) in addition to those described herein that are described merely for exemplary purposes.

A non-planar AMC deposit on a calibration sample is only one of the possible developments that may result in a poor fit between measured and calculated ratios. Other considerations may be that the optical properties of the AMC film are not homogenous as a function of film thickness. Also, for certain values of AMC thickness the reflectance of the AMC/calibration pad film stack may tend to have low values or may even be approaching zero at certain wavelengths. This would provide very little insight as to the intensity of the source of these wavelengths. Another possible reason for a poor fit between measured and calculated ratios may be an inaccurate understanding of the optical properties of the AMC film. The film deposited may consist of many different components, such as discrete layers. It is noted that the non-ideal scattering or non-uniform contaminant film conditions mentioned do not absolutely preclude use of an optical model. Such conditions may, in fact, be well accounted for by use of effective optical parameters for contaminant layers. Hence, the description only becomes unreasonable after some threshold is reached and the use of said effective optical parameters no longer aptly describes the changes in the calibration pad film stack A calibration sample may initially be acceptable, however, may evolve over time to become unacceptable. Alternatively the calibration sample may initially be unacceptable. The cause of contaminates on a sample may be widely varying. For example, a sample may be unacceptable for use if contaminates deposited upon the sample result from inadequately maintaining the purity of the atmosphere in which the sample is kept. Further, mere exposure to light may result in photo-deposition or photo-etch processes that will alter a calibration sample and thus result in a sample being classified as "contaminated." Further, exposure to light may modify the interface bond structure of a sample, thus contaminating the sample for the purposes of calibration. Thus, there are a wide range of mechanisms and causes for a sample being unacceptably contaminated. Further, it is noted that as used herein a "contaminated" sample is not merely one in which a contaminate layer is formed but may also include a sample that has been changed as described above such as from an etch process or bond structure alterations. Alternatively, the properties of a sample may simply change as the sample ages.

Some of the techniques provided herein utilize a calibration pad in which multiple calibration sites are provided. The calibration sites may be formed on the calibration pad in a manner such that the sites provide a multiplicity of the same calibration structure on a single calibration pad. In this manner, a single calibration pad may be provided in an optical metrology tool, however, a plurality of calibration sites of a common calibration structure is now available for use. A particular calibration site may be utilized until that particular site has been determined to become contaminated, in which case the calibration processes may then move to use a different calibration site on the calibration pad. Because multiple sites are provided on the single calibration pad, a new calibration pad need not be utilized. A variety of techniques may be utilized to provide the determination that a site is no longer acceptable for use. Alternatively, the multiple sites may be utilized in such a manner such that each site is only used once or some other set number of times. Further, the plurality of calibration sites that are provided on the single calibration pad may be pre-evaluated so as to initially screen out unacceptable calibration sites prior to use. These sites would not therefore be utilized during calibration processes.

For illustrative purposes and ease of description purposes the term "calibration" is utilized with reference to the samples described herein. However, the concepts described herein are not limited to calibration samples but may also be used for other system characterization samples such as reference samples or standard samples. Thus, it will be recognized that the techniques described herein may be utilized for a wide range of optical tool characterization samples, including but not limited to calibration samples, reference samples and standard samples. The exemplary use of "calibration sample" utilized herein is merely provided for illustrative purposes and may be generically replaced by other optical tool characterization samples for such techniques could equally apply to other characterization samples.

Figure 3:
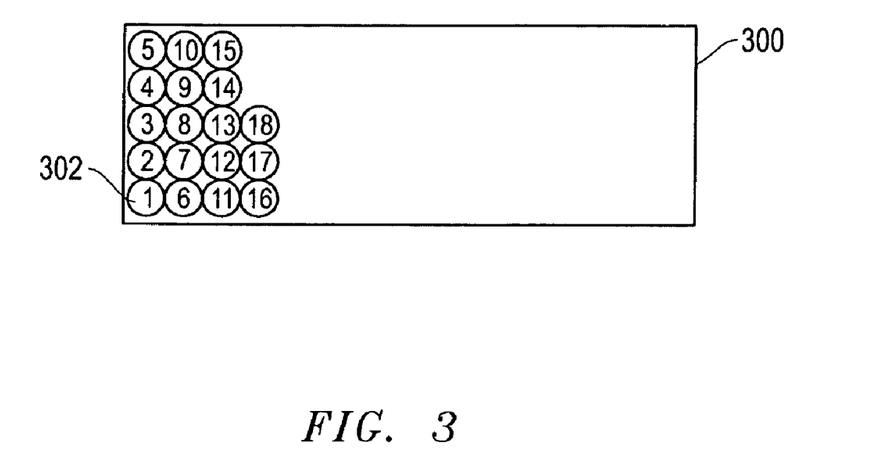
FIG. 3 illustrates a calibration pad with multiple calibration sites.

FIG. 3 illustrates a calibration pad 300 with multiple calibration sites 302 designated. Current optical instruments often possess very small spot sizes and it is conceivable that a small calibration pad could easily provide thousands of potential calibration sites. When certain conditions are met, the instrument automatically advances from a used "bad" calibration site to a new "good" site. The instrument keeps track of all "good" and "bad" sites on the pad and when all sites are presumed "bad" the calibration pad is replaced. In an alternative embodiment, some or all of the sites may undergo some pre-screening characterization and the initially bad sites may be designated as such. Pad replacement would customarily be performed during scheduled maintenance sessions. In this manner a single calibration pad may be utilized for many more calibrations than would be possible if the pad only contained a single calibration site. Movement may thus occur over time from site to site for use in a calibration process. Criteria may be established as to when to move to another site based upon any of a wide range of evaluations, including but not limited to those provided below. Though the designation of a site as "bad" may be based upon measured reflectance data, other criteria may also be used. For example, the number of times a site has been exposed to light may be the criteria for designating a site as bad. Alternatively the cumulative exposure of a site may be the criteria.

Figure 3A:
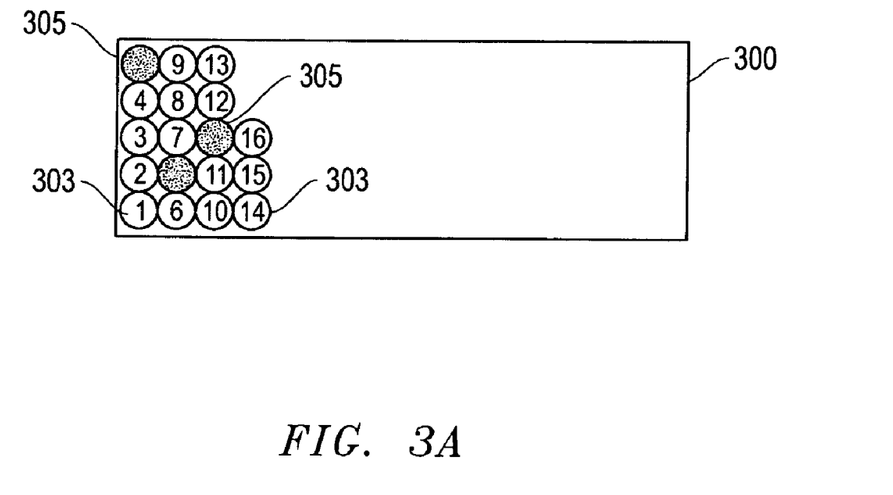
FIG. 3A is an exemplary diagram of a pre-characterized matrix of "good" and "bad" sites on a calibration pad.

FIG. 3A is an exemplary calibration pad with "good" and "bad" calibration sites. The calibration pad 300 has multiple potential calibration sites. The numbered circles 303 represent the "good" sites, while the solid black circles 305 represent the "bad" sites. The "good" sites may be used at a later time to conduct numerous calibration events. It should be noted that the calibration sites may need to be prepared prior to initial characterization and then again before the calibration event in order to ensure that the calibration site remains uncontaminated, or otherwise remains usable. The preparation of a calibration site may involve, but is not limited to, conditioning, exposure and cleaning.

Figure 4:
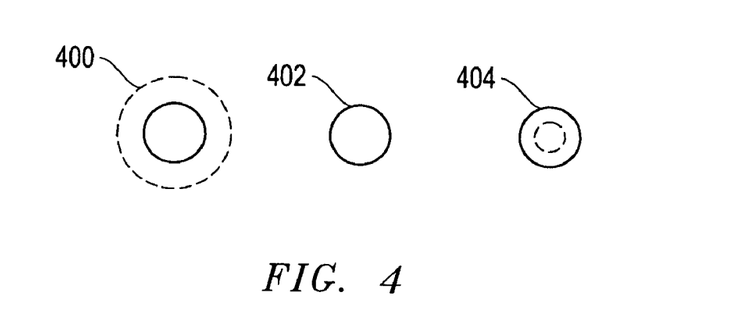
FIG. 4 is a depiction of three different illumination/measurement spot configurations.

The density of the calibration sites on the calibration pad may be impacted by the type of optical spot configuration. In some instances, the illumination and measurement areas of the metrology instrument may be adjusted independently. In such a case, at least three different conditions are possible and these different conditions may influence the nature of the AMC build-up. FIG. 4 illustrates three different spot configurations. Configuration 400 depicts the condition where the dashed illumination spot is larger than the solid measurement spot. Configuration 402 portrays the condition were the illumination and measurement spots are of equal size. And finally, configuration 404 represents the condition where the dashed illumination spot is smaller than the solid measurement spot. It should be noted that in this particular depiction the illumination and measurement spots were circular in nature for illustrative purposes. It is conceivable that either of both of the spots could exhibit other shapes. As the illumination of the sample may have impact on the quality of the sample (for example if the exposure may alter the amount of contamination), then it may generally be desirable that the density of the sites on a pad is such that the illumination spots for adjacent sites do not overlap.

The concepts described herein may be useful for a wide variety of known calibration techniques. For example some techniques involve the use of a single calibration sample while other techniques (such as those mentioned above) utilize two calibration samples and a ratio of the data collected from each sample. The techniques described herein and the use of a calibration pad having multiple calibration sites may be advantageously utilized for techniques that utilize a single calibration sample or techniques that utilize a plurality of calibration samples.

As will be described in more detail below, a wide variety of criteria may be utilized to determine whether a calibration site is good or bad. For example, initial characterization of sites could be accomplished through the use of absolute reflectometry or analytical measurement techniques. Sites may also be characterized based upon whether a calculated contamination thickness from a reflectance or reflectance ratio measurement exceeds some set limit. Further, sites may be characterized based upon the goodness of fit of measured data and calculated data. It will be recognized that the concepts described herein are not limited to the exemplary techniques described to designate a calibration site as good or bad. Such exemplary techniques are now described below, first with respect to an exemplary technique, which relates to calibration methods, which utilize two different calibration samples, and then with respect to a single calibration sample method.

As background, it is known to those in the art that once reflectance data has been recorded from a calibrated reflectometer, it is typically sent to a processor unit where it is subsequently reduced via analytical algorithms. These algorithms generally relate optical data, such as reflectance, to other properties of the sample, which can then be measured and/or monitored like film thickness, complex refractive index, composition, porosity, surface or interface roughness, critical dimensions of patterned features, etc.

Data reduction is generally accomplished using some form of the Fresnel Equations in combination with one or more models to describe the optical properties of the materials comprising the sample. Regardless of the specific model used in the reduction of the data set, the greater goal is generally to use a mathematical expression to describe the measured data such that certain parameters, relating to the properties of the samples (as discussed above), can be obtained through an iterative optimization process. That is, the measured data set is compared to one calculated using an expression that depends on a set of parameters relating to the nature of the sample. The discrepancy between the measured and calculated data sets is minimized by iteratively adjusting the values of the parameters until such time as adequate agreement between the two data sets is achieved. This discrepancy is usually quantified in terms of a "figure of merit" parameter.

Numerous mathematical expressions for calculating figure of merit exist in the prior art. Most of these techniques are to some degree based on a determination of the difference between the measured and calculated spectra. One such technique is the sum of squared residuals normalized by the number of data points (i.e. the un-weighted chi-squared statistic).

A known method of two sample calibration involves the analysis of a reflectance ratio from two calibration samples that results in a determination of the properties of the calibration samples, such as described for example in U.S. Pat. No. 7,282,703 and U.S. patent application Ser. Nos. 10/930,339; 11/418,846 and 11/789,686 the disclosures of which are all expressly incorporated by reference in their entirety to overcome these issues. These techniques may be utilized in conjunction with figure of merit values to characterize the confidence in the calibration procedure. Poor figure of merit values usually indicate less accurate calibration events, while superior figure of merit values are indicative of accurate calibration events. The techniques disclosed herein propose a method that would involve comparing the calibration results to predefined limits in order to determine whether the calibration was successful. If deemed successful, then sample measurements are performed. If the event is unsuccessful, the system automatically moves to the next set of calibration sites on the calibration pads and another attempt is made to calibrate. Other aspects of a calibration event are also taken into account. For example, source failure and hardware issues.

Figure 5:
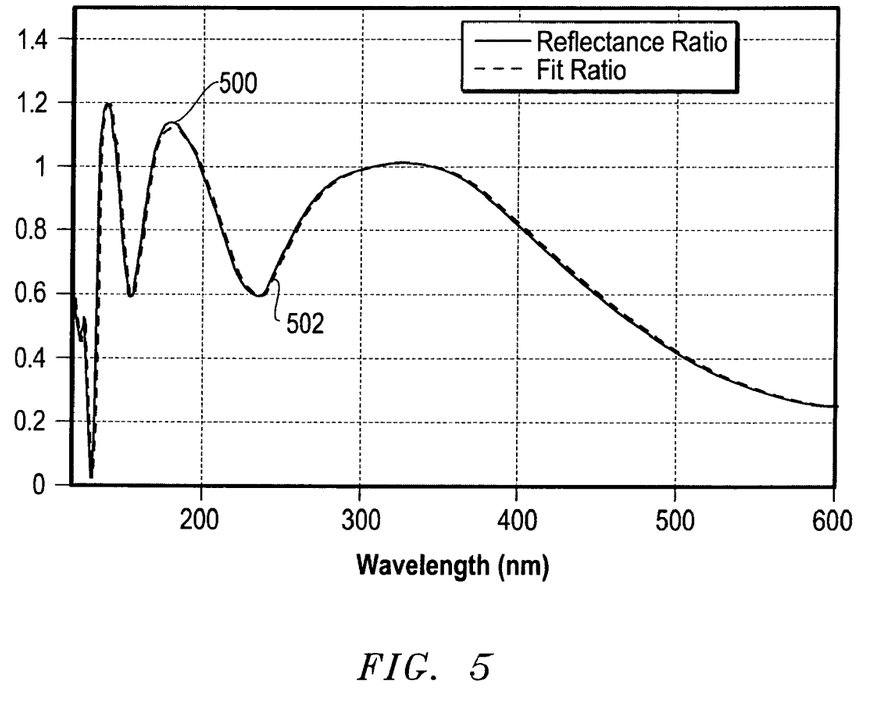
FIG. 5 illustrates measured and calculated calibration pad ratios from "good" sites on calibration pads.

FIG. 5 represents reflectance ratios for "good" sites on calibration pads utilizing a two sample technique in which a reflectance ratio of data from each calibration sample is utilized. The solid curve 500 illustrates a measured reflectance ratio obtained from the two sites. The dashed curve 502 represents the calculated reflectance ratio. The two curves match closely over the wavelength spectral region resulting in a superior figure of merit value. This is indicative of a successful calibration event.

Figure 6:
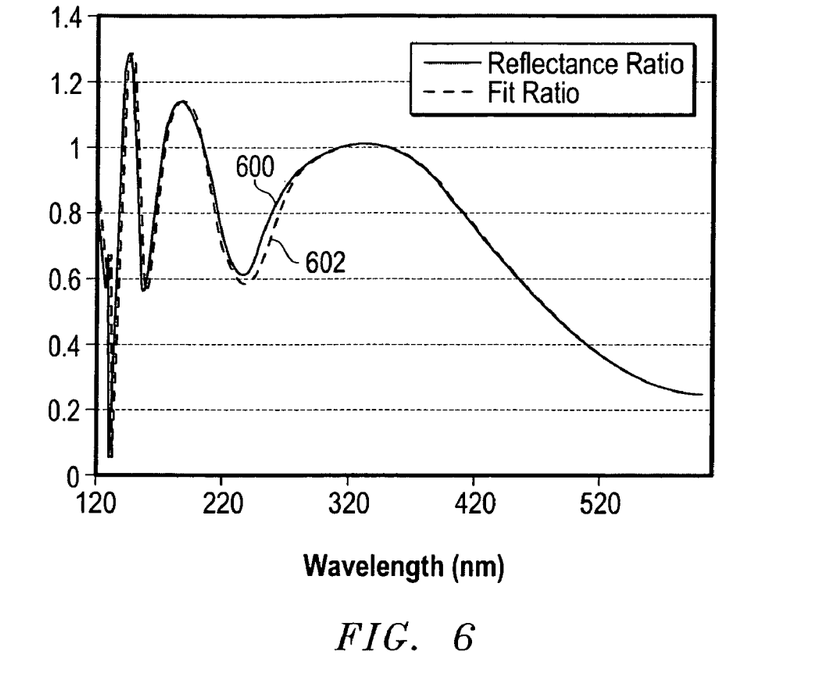
FIG. 6 illustrates measured and calculated calibration pad ratios from "bad" sites on calibration pads.

FIG. 6 is a representation of reflectance ratios for a "bad" site on a calibration pad. The solid line 600 represents the measured reflectance ratio, while the calculated reflectance ratio is illustrated by the dashed line 602. The two curves do not match closely, particularly in the shorter wavelength region of spectra, resulting in a poor figure of merit value. This would be suggestive of an inaccurate calibration event.

Figure 7:
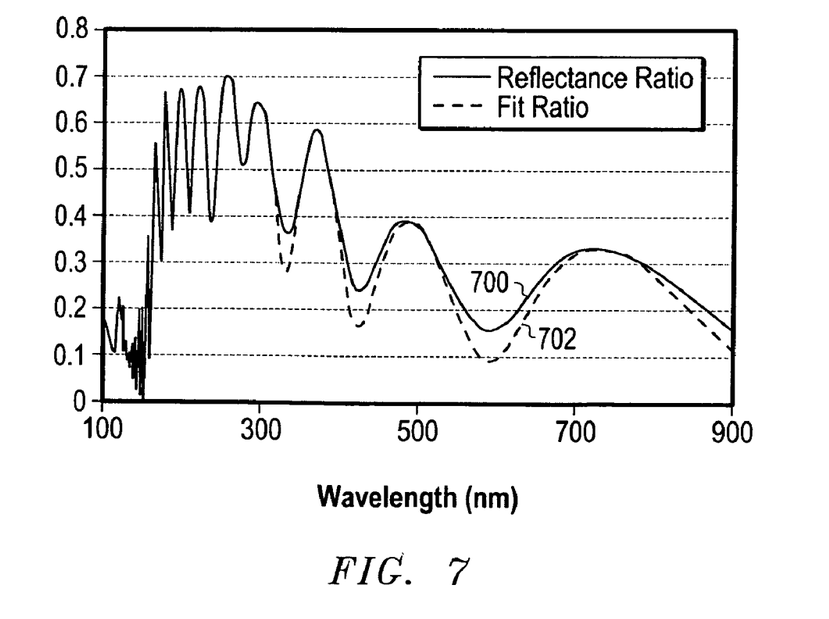
FIG. 7 illustrates measured and calculated calibration pad ratios from "bad" sites on calibration pads.

FIG. 7 illustrates another set of reflectance ratios for a "bad" site on calibration pads. Once again, the solid line 700 represents the measured reflectance ratio, while the calculated reflectance ratio is illustrated by the dashed line 702. In this instance the two curves are significantly different, particularly in the longer wavelength region of the spectra. This discrepancy in the ratio curves is indicative of a poor figure of merit value and therefore, an inaccurate calibration.

Figure 8:
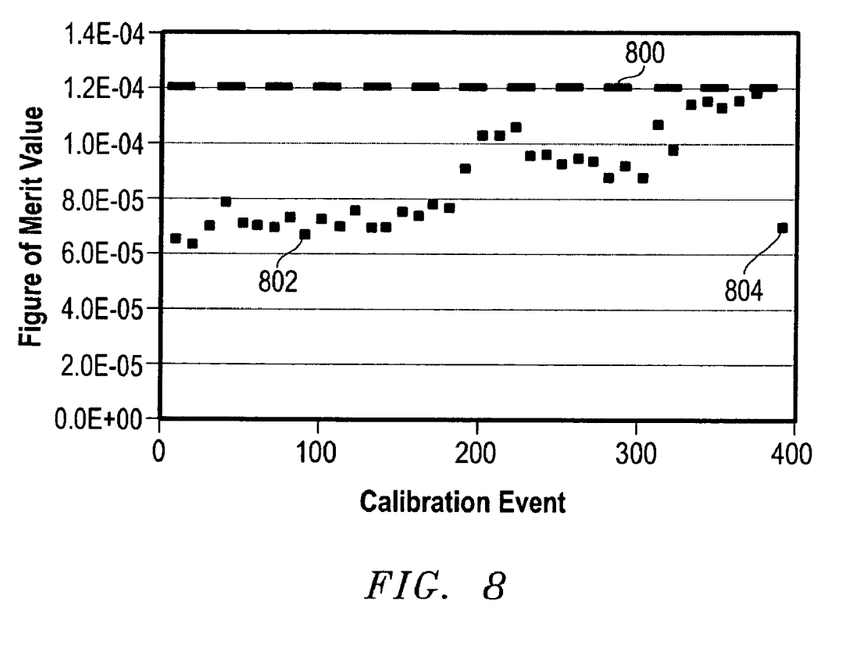
FIG. 8 is an exemplary calibration criterion based on Figure of Merit values as a function of subsequent calibration events.

FIG. 8 is a representation of an exemplary calibration success criterion. The figure of merit values associated with sequential calibration events are recorded. The figure of merit values 802 are observed until the predetermined figure of merit limit 800 is reached. At such time that the limit criterion is met, the system moves to a new set of calibration sites and performs another calibration event. The change in calibration sites is illustrated by the value 804 in FIG. 8. As a result, the figure of merit value drops back down to a level comparable to initial values obtained from previous calibration sites.

Figure 9:
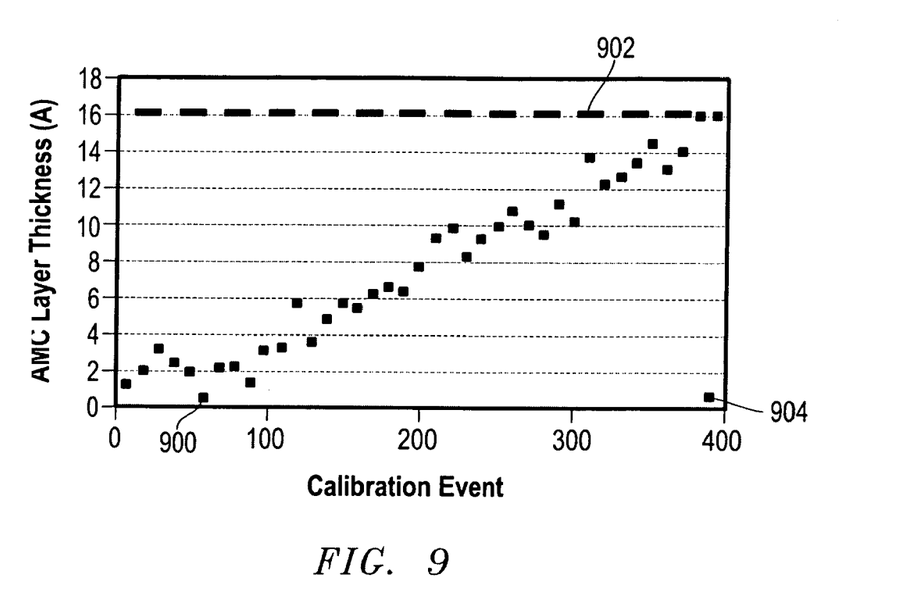
FIG. 9 is an exemplary calibration criterion based on AMC layer thickness values as a function of subsequent calibration events.

Another example of a successful calibration criterion is represented in FIG. 9. The AMC layer thickness values and the effect on subsequent calibration events 900 are documented. It is observable that as the subsequent calibration events occur, the AMC thickness values increase. At such time when the predetermined AMC thickness limit 902 is reached, the system moves to a new set of calibration sites and performs another calibration event. The change to a new calibration site 904 results in the AMC thickness value dropping back down to a level analogous to the initial values obtained from the previous calibration site. Although FIG. 9 sets forth the suggestion that an optimal calibration event is achieved when the AMC thickness value is low, it is conceivable that this may not always be the case. A successful calibration event may be achieved at alternate AMC thickness ranges.

As mentioned above, characterizing the calibrations pads or screening the sites prior to use may further enhance the calibration methodology performance. This method may be utilized to identify "good" and "bad" sites and the bad sites may be skipped so as to yield more accurate calibration results. Also, monitoring and adjusting the exposure dose on the calibration samples by the measurement system may accomplish further performance enhancements. This method may be used to reduce and/or eliminate changes caused by interactions between the illumination of the measurement system and the samples. This would improve the variation between a fleet of tools in an automated semiconductor environment in which exposure dose amongst the fleet may vary.

It is important to consider that certain aspects of the auto-advance calibration methodology described herein may be useful in other embodiments. Such as for example in U.S. Pat. No. 7,126,131, the VUV reflectometer disclosed involved a referencing channel. In this embodiment, the reference plane mirror may be expected to accumulate greater amounts of AMC than other optical surfaces in the system since it is exposed to higher power densities. This is attributed to the mirror being located at the focal plane of a focusing optic. It may be beneficial to mount the reference plane mirror on an x-y stage in the focal plane in order to aid the movement to a different location on the reference mirror, once the contaminants have attained a pre-determined limit. Thus, this is an example in which the concepts described herein may be useful with regard to a reference sample. As noted above, the techniques provided herein may be generally applicable to any optical tool characterization samples, as the example of a calibration sample is meant to be illustrative for all optical tool characterization samples.

Figure 10:
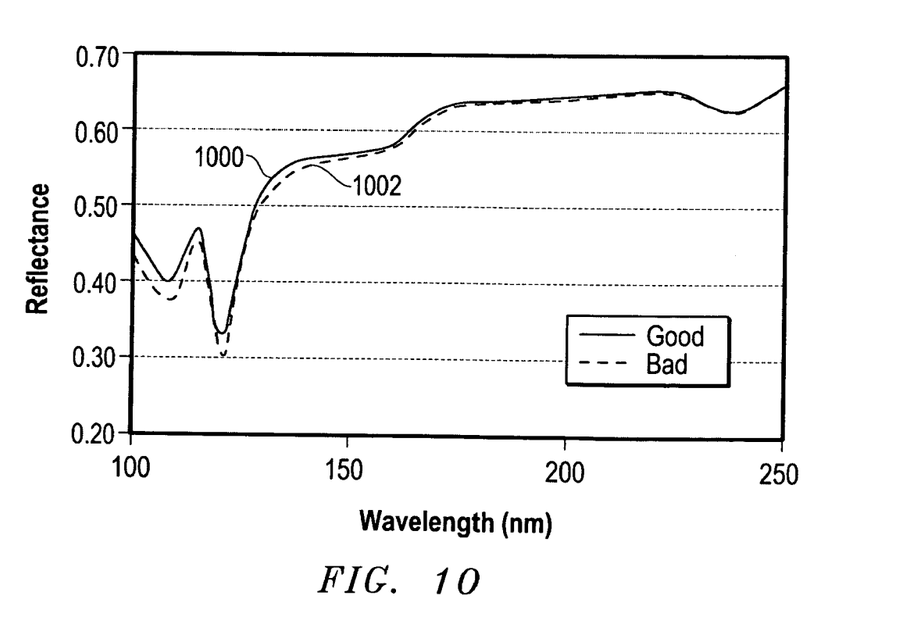
FIG. 10 illustrates reflectance spectra from "good" and "bad" sites in a single site calibration method.

The auto-advance methodology may also be beneficial to improve tool and tool-matching performance through a variety of ways. The data may be exchanged between modules on the same equipment front end module (EFEM) or within the same semiconductor manufacturing fabrication plant located at one site or within several semiconductor manufacturing fabrication plants located at different sites. It would also be advantageous for the data exchange to adjust limits on calibration success criteria based on a module duty cycle or to adjust the illumination conditions on a module-by-module basis in order to better match conditions. Also, matching may occur by controlling the flow of materials and measurements to individual modules to ensure that the calibration pads properties remain synchronized. The improvement of tool and tool-matching performance utilizing the auto-advance methodology is not limited to these particular modifications An alternate choice to exemplary multi-sample techniques described above is the utilization of only a single calibration pad. In one example, this method may involve the usage of one calibration sample whose optical properties are well known and stable (for at least a portion of the wavelength range of the measurement) with respect to time and exposure. Although this assumption may not be completely accurate, it may be reasonable in certain conditions with appropriate calibration sample conditioning. The single calibration pad method may involve pre-characterization, such as collection of reflectance spectra from a group of pre-defined locations on the calibration pad. Pad locations exhibiting significantly different reflectance spectra are discarded from the list of "good" locations to be used in subsequent calibration events. The pre-characterization information for the "bad" sites may also be utilized for adjusting and/or correcting future calibration events from these same sites. Typically the bad sites will have lower reflectance values. FIG. 10 presents reflectance spectra from pre-characterized "good" and "bad" calibration sites. The solid line 1000 represents the "good" calibration sites, while the dashed line 1002 represents the "bad" calibration sites. The line representing the unsuccessful calibration results typically, though not necessarily always, displays lower reflectance values. These lower reflectance values can be attributed to reasons such as thicker contaminant deposits, sample defects, particles on the surface of the sample, etc. The variation between the "good" and "bad" calibration sites as shown in FIG. 10 is typically more prominent at the lower wavelengths.

Some effort is needed in order to determine the absolute reflectance of the calibration sample to be used. This may be achieved using an absolute reflectometer or through some special sample preparation, for example an etch-back of the native oxide on silicon technique. Determination of the absolute reflectance may also be accomplished using an analytical measurement technique, such as transmission electron microscopy (TEM), atomic force microscopy (AFM), scanning electron microscopy (SEM), x-ray methods, etc. Alternately, a reflectance ratio or multiple reflectance ratios can be used for a single determination of the absolute reflectance of the calibration sample.

The advantage of this approach is that it may yield higher stability. This is due to the fact that a fitting/analysis step is not involved. Disadvantages include less insight into accuracy. The method is unable to determine whether the sites have changed since the pre-characterization, and, the system is less capable of indicating "errors" such as identifying problems with calibration pads, sources, signal levels, mechanical alignments, etc.

It is noteworthy that the calibration success criteria may be based on a single result of a calibration event or any combination of results from multiple calibration events. Although figure of merit values and AMC thickness values have been presented as factors for determining calibration success, it is notable that many other possibilities exist and may be utilized equally as well. Further, the mere frequency that the calibration site needs to be changed may be indicative of a sample and/or environmental cleanliness condition. These conditions may be monitored and used to adjust and/or enhance tool-cleaning parameters in order to establish optimum tool maintenance, such as for example in U.S. Pat. No. 7,342,235 and U.S. patent application Ser. Nos. 11/600,414 and 11/600,477, the discloses of which are all expressly incorporated by reference in their entirety to overcome these issues.

The calibration site change frequency may be expected to be influenced and/or impacted by tools, processes, samples, or conditions in the neighboring vicinity of the calibration samples. It follows that calibration site change frequency may be monitored and used to identify significant events or activities which could be expected to impact other events or activities within a manufacturing environment. For example, it is conceivable that activities conducted on certain process tools could result in a change in the contamination level of the environment within a manufacturing facility and that these changes could adversely affect product yield. If a correlation between the occurrence of such activities and the calibration site change frequency could be established, then the calibration site change frequency could be monitored in order to identify such occurrences and enable action to be taken in order to reduce yield impact. In this sense monitoring of the calibration site frequency could provide valuable feedback to manufacturing organizations in order to assist with yield improvement.

The pre-characterization technique described above may be used on its own or in conjunction with the dual sample methods described above or other methods that monitor changes over time. When used in combination with the dual sample method, a preferred embodiment may involve performing an initial successful dual sample calibration, and then utilizing the calibrated instrument to pre-characterize a series of pre-defined locations on the calibration pads. Thus, the technique involves making an initial identification of "good" and "bad" calibration sites. In this way, a separate metrology tool is not needed to pre-characterize the sites. Determination is made of at least one property of "good" calibration sites and accumulated for future use in performing a dual pad calibration. Finally, one may also use the stored pre-characterization data to aid in determination of dual pad calibration results. This pre-characterization data should improve the stability of the dual sample calibration method since fewer properties of the dual pad calibration samples would be determined during the calibration process.

An alternative method to the combined dual sample and single pad methods described above would be to pre-characterize samples of a dual sample technique, and then to use the ratio to determine if a site has altered over time, by comparing subsequent data to the stored ratio for that site. If no change has occurred, a single pad calibration may then be performed.

The techniques described above provide a wide range of means to evaluate a calibration site so as to determine if the calibration site is acceptable for either initial or further use. It will be recognized that for calibration methods in which two different calibration sample sites are utilized in the calibration process, one site and/or both sites may be determined to be unacceptable for use. In some methods in which two sample sites are utilized, it may not be possible to distinguish which particular site is unacceptable for use and thus both sites may be designated as "bad" even though it may be possible that only one of the two calibration sites is actually unacceptable.

It may be desirable to perform the characterization of a site, whether a pre-characterization, or an analysis such as the dual sample techniques described above, after the site has "aged" in a system for some period. Thus, when a pad is first placed in a system the pad may exhibit some initial settling changes after which relative equilibrium is reached. Thus, changes in the site, which occur during an initial period of time, may not be mistaken for system changes.

The technique disclosed herein regarding automated calibration is advantageous for use with a wide range of optical metrology tools. For example, as described herein the techniques may be used with VUV reflectometers. However, it will be recognized that these concepts are not just limited to the VUV spectral range and not just limited to use with reflectometers. Rather other wavelengths and other optical metrology tools may advantageously utilize the concepts disclosed herein.

Further modifications and alternative embodiments of the techniques described herein will be apparent to those skilled in the art in view of this description. It will be recognized, therefore, that the techniques described herein are not limited by these example arrangements. Accordingly, this description is to be construed as illustrative only and is for the purpose of teaching those skilled in the art the manner of carrying out the techniques described herein. It is to be understood that the forms of the techniques described herein shown and described are to be taken as the presently preferred embodiments. Various changes may be made in the implementations and architectures. For example, equivalent elements may be substituted for those illustrated and described herein and certain features of the techniques described herein may be utilized independently of the use of other features, all as would be apparent to one skilled in the art after having the benefit of this description of the techniques.

What is claimed is:

1. A method of evaluating an optical metrology tool, comprising:
   utilizing an optical tool characterization pad for use in assisting in the evaluation of an optical metrology tool;
   providing multiple characterization sites of a similar characterization structure upon the characterization pad; and
   designating at least some of the characterization sites as either acceptable for use or not, wherein based upon the designation, after the designation at least some of the characterization sites are not utilized for evaluation of the optical metrology tool.

2. The method of claim 1, wherein a single pad calibration process is utilized.

3. The method of claim 1, wherein a dual pad calibration process is utilized.

4. The method of claim 1, wherein the optical metrology tool is a reflectometer.

5. The method of claim 1, wherein the designation of sites as acceptable for use or not is based at least in part upon an initial pre-characterization of the characterization pad.

6. The method of claim 1, wherein the designation of sites as acceptable for use or not is based, at least in part, upon a determination made after at least some use of the characterization pad.

7. The method of claim 6, wherein upon determination of a first characterization site being not acceptable for use, a second characterization site is subsequently utilized.

8. The method of claim 7, wherein the optical metrology tool automatically moves from the first characterization site to the second characterization site upon determination of the first characterization site being not acceptable for use.

9. A method of calibrating an optical metrology tool, comprising:
   providing a calibration pad for use in a calibration process of the optical metrology tool;
   partitioning the calibration pad into a plurality of calibration sites, the calibration sites having similar calibration structures;
   utilizing a first calibration site of the calibration pad for calibrating the optical metrology tool;
   detecting that the first calibration site does not satisfy a criteria for use of the first calibration site; and
   switching from use of the first calibration site to use of a second calibration of the calibration pad for calibrating the optical metrology tool based upon the detection of the first calibration site not satisfying the criteria.

10. The method of claim 9, wherein the criteria is based on reflectance ratio data.

11. The method of claim 10, wherein the switching from use of the first calibration site to use of a second calibration of the calibration pad is based upon a calculated contamination thickness exceeding a predetermined set limit, the calculated contamination thickness being obtained by using reflectance ratio data.

12. The method of claim 9, wherein the criteria is based upon a figure of merit value.

13. The method of claim 12, wherein the figure of merit value is indicative of calibration accuracy.

14. The method of claim 9, wherein the criteria is based upon a calculated airborne molecular containment thickness.

15. The method of claim 9, wherein contamination of the calibration pad varies as the sample pad ages.

16. The method of claim 9, wherein contamination of the calibration pad varies from multiple uses of the calibration pad.

17. The method of claim 9, wherein a frequency of calibration site changes may be indicative of a sample and/or environmental cleanliness condition.

18. The method of claim 9, wherein monitoring of the frequency of calibration site changes may provide feedback regarding a manufacturing process.

* * * * *